United States Patent
Naidu (10) Patent No.: US 10,588,547 B2
(45) Date of Patent: Mar. 17, 2020

(54) SYSTEMS, DEVICES AND METHODS RELATING TO MOTION DATA

(71) Applicant: InMotion, LLC, Irvine, CA (US)

(72) Inventor: Srini G. Naidu, Northville, MI (US)

(73) Assignee: InMotion, LLC, Irvine, CA (US)

( * ) Notice: Subject to any disclaimer, the term of this patent is extended or adjusted under 35 U.S.C. 154(b) by 327 days.

(21) Appl. No.: 15/513,193

(22) PCT Filed: Oct. 6, 2015

(86) PCT No.: PCT/US2015/054253
§ 371 (c)(1),
(2) Date: Mar. 22, 2017

(87) PCT Pub. No.: WO2016/057521
PCT Pub. Date: Apr. 14, 2016

(65) Prior Publication Data
US 2017/0296106 A1    Oct. 19, 2017

Related U.S. Application Data (60) Provisional application No. 62/060,337, filed on Oct. 6, 2014.

(51) Int. Cl.
*A61B 5/11* (2006.01)
*A61B 90/98* (2016.01)
*A61B 5/00* (2006.01)

(52) U.S. Cl.
CPC .......... *A61B 5/1126* (2013.01); *A61B 5/1112* (2013.01); *A61B 5/1121* (2013.01);
(Continued)

(58) Field of Classification Search
CPC ... A61B 5/1126; A61B 5/1112; A61B 5/1121; A61B 5/6807; A61B 5/7267;
(Continued)

(56) References Cited

U.S. PATENT DOCUMENTS

2006/0184336 A1*  8/2006  Kolen ................ G01C 19/00
                                                     702/150
2007/0219744 A1    9/2007  Kolen
(Continued)

FOREIGN PATENT DOCUMENTS

WO    WO-2014138007 A1    9/2014

OTHER PUBLICATIONS

Mannini, Andrea et al., "Accelerometry-Based Classification of Human Activities Using Markov Modeling," Hindawi Publishing Corporation, Computational Intelligence and Neuroscience, vol. 2011, Article ID 647858, 11 pages.
(Continued)

*Primary Examiner* — Toan M Le
(74) *Attorney, Agent, or Firm* — Panagos Kennedy PLLC; Bill C. Panagos; Linda D. Kennedy (57) ABSTRACT

Systems for studying motion are provided. A computing device [10] has a processor [20], an accelerometer [11], a gyroscope [12], a magnetometer [13] and storage/computer readable media [30] in communication with one another. The computing device [10] can sense, classify, qualify and/or quantify real-time motion data of a moving target against classified initial motion data in a motion library [32]. Motion data is processed as particularized units of motion. The computing device [10] may use machine learning algorithms for "training" and "learning." The computing device [10] can be used in many industries, including the fitness industry, where computing device [10] can be used with wearable technology.

17 Claims, 6 Drawing Sheets

(52) U.S. Cl.
CPC .......... *A61B 5/6807* (2013.01); *A61B 5/7267* (2013.01); *A61B 5/7278* (2013.01); *A61B 5/742* (2013.01); *A61B 90/98* (2016.02); *A61B 2562/0219* (2013.01); *A61B 2562/0223* (2013.01)

(58) Field of Classification Search
CPC ....... A61B 5/7278; A61B 5/742; A61B 90/98; A61B 2562/0219; A61B 2562/0223; G06K 9/00342; G06K 9/00348
See application file for complete search history.

(56) References Cited

U.S. PATENT DOCUMENTS

| | | |
|---|---|---|
| 2008/0284650 A1 | 11/2008 | MacIntosh et al. |
| 2013/0053190 A1 | 2/2013 | Mettler |
| 2014/0114453 A1 | 4/2014 | Bentley |
| 2014/0135150 A1 | 5/2014 | Thurman et al. |

OTHER PUBLICATIONS

Baca, Arnold, "Methods for Recognition and Classification of Human Motion Patterns—A Prerequisite for Intelligent Devices Assisting in Sports Activities," University of Vienna, Wien, 7 pages, 2012.
Zhang, Mi, et al., "Motion Primitive-Based Human Activity Recognition Using a Bag-of-Features Approach," IHI'12, Jan. 28-30, 2012, 10 pages.
Apple Watch, Activity or Workout Apps., "Calibrating your Apple Watch for improved Workout and Activity accuracy," Jul. 6, 2015, 2 pages.
Bao, Ling et al., "Activity Recognition from User-Annotated Acceleration Data," Massachusetts Institute of Technology, Pervasive 2004, LNCS 3001, pp. 1-17, 2004, 17 pages.
Dernbach, Stefan et al., "Simple and Complex Activity Recognition Through Smart Phones," Department of Computer Science, Whitworth University, Spokane, USA, 8 pages.
Longstaff, Brent et al., "Improving Activity Classification for Health Applications on Mobile Devices using Active and Semi-Supervised Learning," Pervasive Health 2010, 8851, 7 pages.
Rodriguez-Silva, D.A., et al., "Human Motion Tracking and Gait Analysis: a Brief Review of Current Sensing systems and Integration with Intelligent Environments," VECIMS 2008—IEEE international Conference, Istambul, Turkey. Jul. 14-16, 2008, 6 pages.
Bedogni, Luca, et al., "By Train or by Car? Detecting the User's Motion Type through Smartphone Sensors Data," Italian Ministry of University and Scientific Research, 13 pages.
Chernbumroong, Saisakul, et al., "Activity classification using a single wrist-worn accelerometer," College of Arts, Media and Technology, Chiang Mai University, Chiang Mai, Thailand, 6 pages, 2011.
Kwapisz, Jennifer, et al., "Activity Recognition using Cell Phone Accelerometers," SIGKDD Explorations vol. 12, Issue 2, pp. 74-82, 9 pages, 2010.
Saponas, T. Scott, et al., "iLearn on the iPhone: Real-Time Human Activity Classification on Commodity Mobile Phones," University of Washington, Seattle, WA, 4 pages, 2008.
Stikic, Maja, et al., "Exploring Semi-Supervised and Active Learning for Activity Recognition," Fraunhofer IGD, Germany, 8 pages, 2008.
UP3, Jawbone, https://jawbone.com/store/buy/up3?color=silver, 10 pages, 2015.
Varkey, John Paul, et al., "Human motion recognition using a wireless sensor-based wearable system," Published online: Sep. 11, 2011, Springer-Verlag London Limited 2011, Pers Ubiquit Comput, DOI 10.1007/s00779-011-0455-4, 14 pages.
Zibreg, Christian, "How to calibrate Apple Watch for accurate Workout and Activity tracking," May 12, 2015, iDownloadBlog 2015, 9 pages.
Hemminki, Samuli, et al., "Accelerometer-Based Transportation Mode Detection on Smartphones," Helsinki Institute for Information Technology HIIT, 2013 ACM 978-1-4503-2027—Jun. 13, 2011, http://dx.doi.org/10.1145/2517351.2517367, 14 pages.
Wu, Wanmin, et al., "Classification Accuracies of Physical Activities Using Smartphone Motion Sensors," J Med Internet Res 2012, Published May 10, 2012 vol. 14, No. 5 (2012), Sep.-Oct, 13 pages.
Öhberg, Fredrik, et al., "Comparative analysis of different adaptive filters for tracking lower segments of a human body using inertial motion sensors," 2013 IOP Publishing Ltd., Meas Sci. Technol. 24 (2013) 085703, 12 pages.
Ayrulu-Erdern, Birsel, et al., "Leg Motion Classification with Artificial Neural Networks Using Wavelet-Based Features of Gyroscope Signals," Sensors 2011, 11(2), 1721-1743, doi: 10.3390/s110201721, 19 pages.
Blind Motion Project, Machine learning in navigation devices: detect maneuvers using accelerometer and gyroscope, Apr. 11, 2015, http://blindmotion.github.io/2015/04/11/ml-in-navigation/, 16 pages.
Freedson, Patty S., et al., "Evaluation of artificial neural network algorithms for predicting METs and activity type from accelerometer data: validation on an independent sample," Journal of Applied Physiology, Dec. 1, 2011, vol. 111, No. 6, 1804-1812, 18 pages.
Yang, Che-Chang, et al., "A Review of Accelerometry-Based Wearable Motion Detectors for Physical Activity Monitoring," Sensors 2010, 10(8), 7772-7788; 17 pages.
Jonathan Muckell et al: "Algorithms for compressing GPS trajectory data", Advances in Geographic Informtion Systems, ACM, 2 Penn Plaza, Suite 701, New York NY 10121-0701 USA, Nov. 2, 2010 (Nov. 2, 2010), pp. 402-405, XP058229949, DOI: 10.1145/1869790.1869847 ISBN: 978-1-4503-0428-3.
Juan Carlos Castro-Palacio, et al: "Using a mobile phone acceleration sensor in physics experiments on free and damped harmonic oscillations", American Journal of Physics, vol. 81, No. 6, Jun. 30, 2013 (Jun. 30, 203), pp. 472-475, XP055471158.
Chun Zhu et al: "Multi-sensor fusion for human daily activity recognition in robot-assisted living", Human-Robot Interaction (HRI), 2009 4th ACM/IEEE International Conference on, IEEE, 2 Penn Plaza, Suite New York NY 10121-0701 USA, Mar. 11, 2009 (Mar. 11, 2009), pp. 303-304, XP032214637,DOI: 10.1145/1514095.1514187; ISBN: 978-1-60558-404-1.
Evans R Let Al: "Detection of Gait Phases Using Orient Specks for Mobile Clinical Gait Analysis", 2014 11th International Conference on Wearable and Implantable Body Sensor Networks, IEEE, Jun. 16, 2014 (Jun. 16, 2014), pp. 149-154, XP032620706, DOI: 10.1109/BSN.2014.22.
European Office Action, dated Oct. 23, 2019.

\* cited by examiner

X-Acceleration
FIG. 4A

Y-Acceleration
FIG. 4B

Z-Acceleration
FIG. 4C

X-Angular Rate
FIG. 4D

Y-Angular Rate
FIG. 4E

Z-Angular Rate
FIG. 4F

X-Magnetometer
FIG. 4G

Y-Magnetometer
FIG. 4H

Z-Magnetometer
FIG. 4I

Action Classes

Basketball

Tennis

Boxing

Action engine detected: Boxing with 98% accuracy

Duration: 3.0 minutes

Offense:
Jabs thrown: 11
Upper cuts thrown: 3
Left hooks thrown: 4
Right crosses thrown: 3
Combos thrown (less than 3 secs between punches): 3

Defense:
Head hits taken: 2
Body hits taken: 5
Falls: 0

Compared to average:
15% More punches thrown per minute
10% fewer head hits taken
12% fewer body hits taken

FIG. 9

SYSTEMS, DEVICES AND METHODS RELATING TO MOTION DATA

RELATED APPLICATIONS

This application claims the benefit of and priority to PCT Application No. PCT/US2015/054253, filed Oct. 6, 2015 and U.S. Provisional Patent Application No. 62/060,337, filed Oct. 6, 2014, which are hereby incorporated by reference in their entireties.

TECHNICAL FIELD

This disclosure relates to systems, devices and methods relating to the analysis of motion. Motion is, as used herein, any quantifiable movement in 3D space relative to time. Systems and devices may include hardware and software systems, include ng but not limited to those adapted for use in wearable technologies.

BACKGROUND

Across many industries, it is useful to study the motion of a moving target, and to use a resultant analysis of the motion to improve performance of the moving target. In the case where a human being is a selected moving target, for example, the fitness industry and the health industry (e.g., physical therapy and occupational therapy) may find the study of certain human motions beneficial and advantageous.

Various techniques are known for sensing motion in real time, including using a variety of sensors that can be affiliated with the moving target. Some exemplary sensors include accelerometers, gyroscopes, and other devices. A moving target may be any of a number of objects. For example, a moving target may be all or part of an animal, including a human, a horse, a dog, a bird, or a fish or other animals. A moving target may be all or part of a vehicle, including an automobile, aircraft, spacecraft, ships, trucks, recreational vehicles, and more. A moving target may also be a robotic apparatus, or machine componentry with moving parts. A moving target can even be a missile.

Certain existing motion sensing and processing systems provide users a way to analyze data by comparing real-time data to statistical models representing certain types of known motions. Some such systems additionally include machine learning algorithms, capable of updating the statistical models based on real-time sensed motion data. Unfortunately, systems relying on statistical models in lieu of actual data for comparison purposes lose information about the data by reliance on statistics. That loss can limit what can be compared and what can be analyzed, especially in the quantification of real-time motion data. Certain existing systems for motion analysis also lack accuracy due at least in part by reliance on statistics rather than reliance on actual data for comparison.

Accurate and efficient systems, devices and methods for analyzing motion, in terms of qualification and quantification, are needed.

SUMMARY

It has been discovered that data from signals relating to motion received from sensors can be processed in particular units of motion, the contents of which provide qualitative and quantitative information about the real-time motion when compared to data in a motion library.

Such units of motion, when populated with data, can be classified into predetermined motion classes such as walking, jumping, etc. A combination of motions can further be classified into more complex action classes, such as playing tennis, boxing, etc. Contents of real-time action data, processible as units of motion, can provide qualitative and quantitative information about the real-time action when compared to data in an action library.

In one embodiment, a motion library and an action library each include actual measured data processible in units of motion rather than statistical models representing actual data. This way, data integrity may be maintained and, surprisingly, performance of analysis of such data is efficient and accurate.

The unit of motion described in this disclosure is an equation that is a function of a plurality of equations. The number of equations feeding into the unit of motion is the same number of the degrees of freedom being sensed by a sensing system. The degrees of freedom and the time interval are predetermined, depending upon the application. By way of non-limiting example, in an application for analyzing human athletic activity, if nine degrees of freedom are being measured (acceleration, gyro and magnetometer data each in X, Y and Z directions) over intervals of 50 ms, then each unit of motion includes 450 data points x. The content of a particular unit of motion may be uniquely identifiable with a particular class of motion.

These units of motion allow fast processing of motion data by a processor, and efficient and accurate comparison of real-time motion data to actual initial motion data. The efficiency may be due to the retention of "strength" information S (sometimes referred to as "weight" information in machine learning literature) affiliated with each data point x in the unit of motion during machine learning. S allows for a compact representation of motion. Strength information S in certain literature describing prior art machine learning applications for motion is discarded after classification. In spite of the general teachings to discard S in motion study applications, it has been discovered that retention of the strength information S may assist in the efficiency/speed of qualitative comparison between real-time motion data and initial motion data by providing information to an algorithm about which motion data to ignore because of a high cost, and which low cost motion data to further analyze for quantification. The retention of S not only allows for efficiency/speed but also provides information on the x values that is of importance for the particular classes of motions to be included in the qualification/quantification steps, thus improving accuracy.

This processing of units of motion as described herein provides qualification and quantification of real-time motion data, which can be based at least in part on the comparison with initial motion data. Systems, devices and methods using these units of motion for motion analysis and action analysis are suitable for any number of applications across a broad range of industries, both civilian in nature and military in nature.

DETAILED DESCRIPTION

All figures and examples herein are intended to be non-limiting; they are mere exemplary iterations and/or embodiments of the claims appended to the end of this description. Modifications to system, device, the order of steps in processes, etc, are contemplated.

Figure 1:
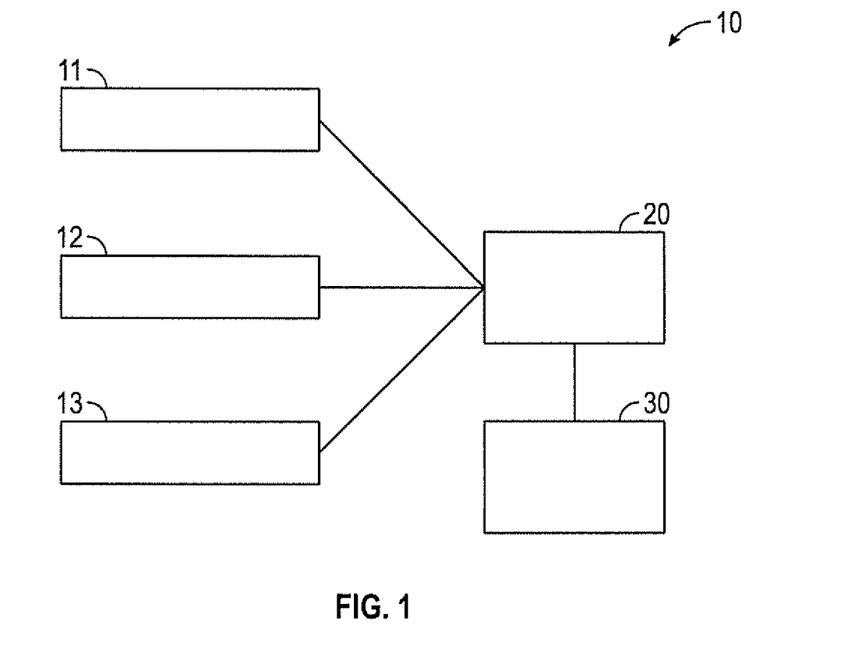
FIG. 1 is a schematic of an exemplary computing device.

Referring to FIG. 1, a schematic of an exemplary computing device 10 is depicted. Computing device 10, as depicted, includes a sensing system that uses a plurality of sensing devices for sensing motion. As depicted, the plurality of sensing devices includes accelerometer 11, gyroscope 12 and magnetometer 13. Other motion sensing and other sensing devices may be included, depending on the nature of the motion and other information to be analyzed, qualified and quantified. Some or all of the sensing devices may be combined into a single inertial measurement unit (IMU).

Exemplary motion sensing devices may include but are not limited to commercially available IMUs, accelerometers, gyroscopes, magnetometers, global positioning (GPS) sensors, RFID sensors, or other sensors. Other microelectromechanical (MEMS) sensors may be incorporated into a sensing system compatible with the disclosed computing device, including digital compasses, inertial modules, pressure sensors, humidity sensors and microphones. Still other sensors or sensing systems or devices may be used in connection with computing device 10, including one or more of smart sensors and sensor hubs, UV index sensors, temperature sensors and touch sensors. Contemplated sensors include those commercially available from STMicroelectronics of Geneva, Switzerland. Sensor fusion is also contemplated for use with the sensing system. A sensing system may wirelessly communicate with other components of computing device 10. Such communication may involve any of a number of protocols, including ANT, ANT+, Bluetooth, BlueRobin and/or others.

As depicted, exemplary motion sensing devices 11, 12 and 13 generate at least one signal to be processed into data using commercially available hardware and standard software protocols, as would be appreciated by those of ordinary skill in the art. For example, an analog signal may be subjected to an anti-aliasing filter, converted into digital data, and run through at least one or more digital filter stages such as a Bessel and/or a Butterworth filter. Thus, since sensors send signals, the transmission of data from sensors may be indirect in that there is intermediate processing of the signal before motion data is available for processing by the processors and computer programs disclosed herein as units of motion.

In the depicted example, accelerometer 11 transmits, directly or indirectly, acceleration data in the X, Y and Z direction. Gyroscope 12 transmits, directly or indirectly, angular velocity data in the X, Y and Z direction. Magnetometer 13 transmits, directly or indirectly, orientation data in the X, Y, and Z direction.

The motion data transmitted by a sensing system including one or more sensing devices is processed by processor 20 using at least one computer program. Although drawn as a unitary box schematically, it is contemplated that processor 20 may be representative of a group of processors in communication with one another via a network. The processor 20 runs a computer program in an operating system running in memory/computer readable media 30. Again, although drawn as a unitary box schematically, it is contemplated that memory/computer readable media 30 may be at least in part remote from and in communication with a device (such as a wearable patch or housing attachable to or embedded in clothing, or a watch or glasses) containing a computing device 10.

Computing device 10 and/or certain of its components, as would be appreciated by those of ordinary skill in the art, may operate using one or more power sources. In some embodiments, power sources may be rechargeable. Recharging may occur by, for example, a cable attached to a charging source or by inductive charging.

Figure 2:
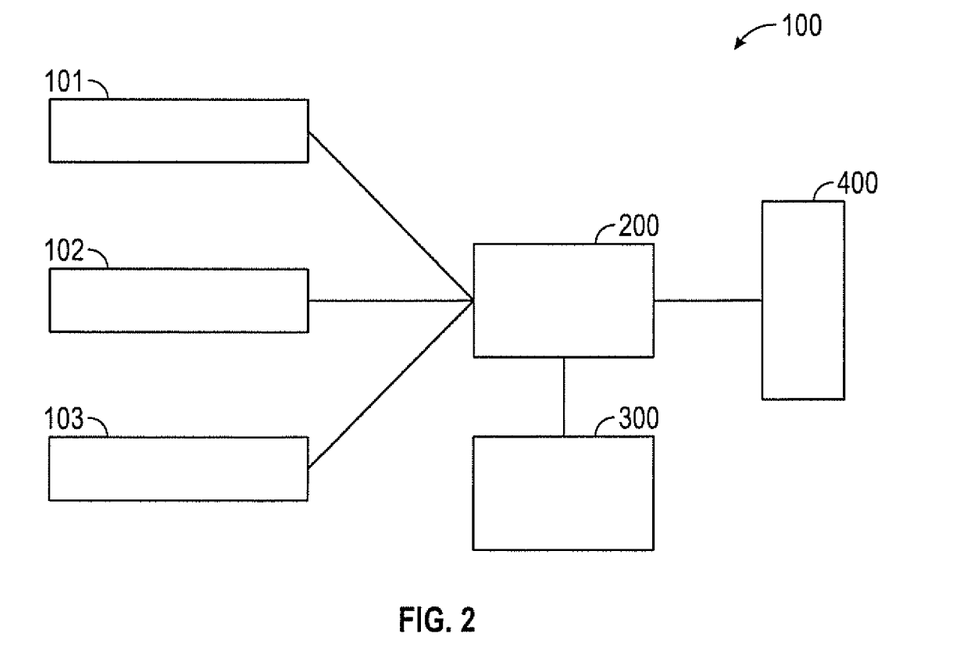
FIG. 2 is a schematic of an exemplary computing device.

Referring to FIG. 2, a schematic of another exemplary computing device 100 is depicted. Computing device 100, as depicted, includes a plurality of sensing devices for sensing motion. Accelerometer 101, gyroscope 102 and magnetometer 103 are illustrated by way of non-limiting example. The resulting motion data extracted from the signals is processed by the processor 200 using software running in memory/computer readable media 300. Computing device 100 is different from computing device 10 in that it also includes a display 400. Any number of local or remote display systems and devices may be suitable for use with computing device 100. For example, a display can be a screen such as one directly on a wearable watch, a projection that may appear on glasses, or display 400 can be a remote computer screen or monitor on a computing device such as a smartphone, a laptop, a tablet or a desktop computer. The display can also be integrated with another software program, including commercially available applications running in typical operating systems. For example, it is contemplated that output from the computing device 100 could be visible through an application for a mobile phone. Such application, in the case of a human being, could be a mapping application or fitness application. In the case of a robot or vehicle, the display might appear as output through a separate but compatible diagnostic program in communication with computing device 100.

Figure 3:
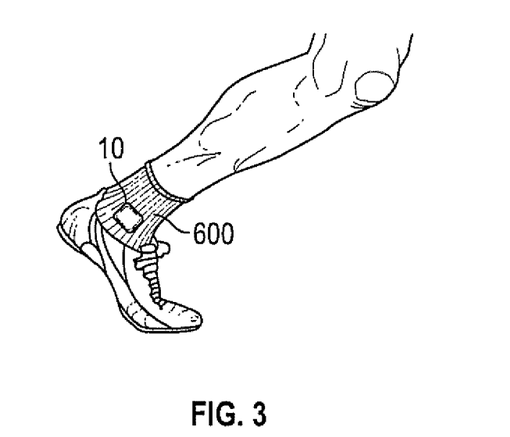
FIG. 3 is an exemplary computing device on a moving target.
Figure 4A:
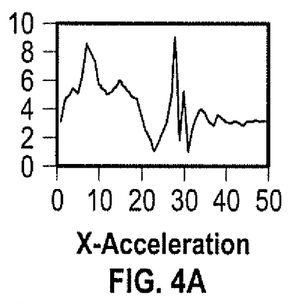
FIGS. 4A-4C are exemplary signals from an accelerometer.
Figure 4B:
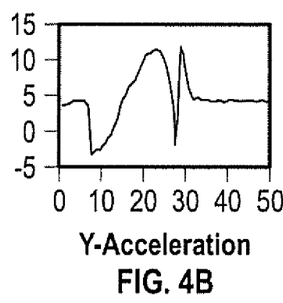
Figure 4C:
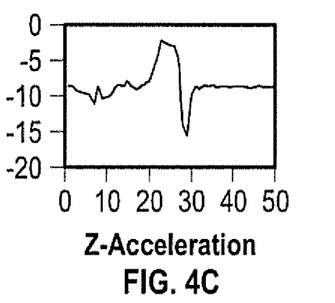
Figure 4D:
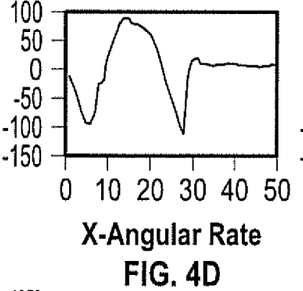
FIGS. 4D-4F are exemplary signals from a gyroscope.
Figure 4E:
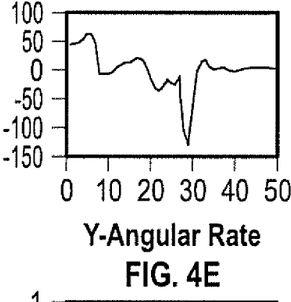
Figure 4F:
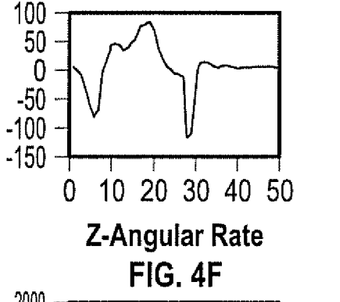
Figure 4G:
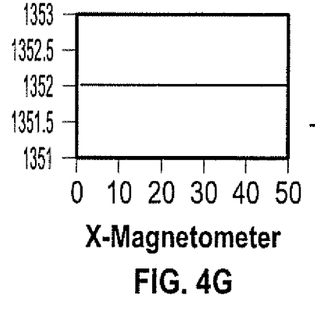
FIGS. 4G-4I are exemplary signals from a magnetometer.
Figure 4H:
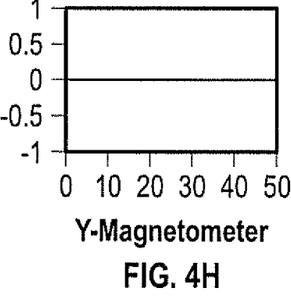
Figure 4I:
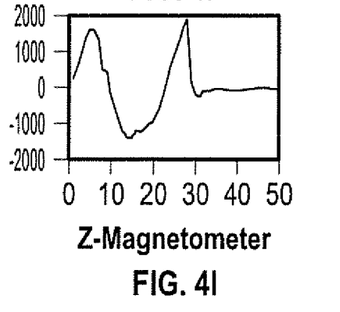

Referring to FIG. 3, an exemplary computing device 10 is attached to a moving target. In the non-limiting depiction, the moving target is a human being and the computing device 10 is incorporated into a wearable device (a sock 600) attached indirectly to the human being by being removably placed on the human being's foot. Attachment can be direct or indirect, removable attachment, permanent attachment, integral formation, etc. Attachment can include mechanical devices such as clips and hook and loop fasters and/or adhesives. As noted above, a moving target may be any of a number of objects. For example, a moving target may be all or part of an animal, including a human, a horse, a dog, a bird, or a fish or other animals. A moving target may be all or part of a vehicle, including an automobile, aircraft, spacecraft, ships, trucks, recreational vehicles, and more. A moving target may also be a robotic apparatus, or machine componentry with moving parts. A device incorporating some or all of computing device 10, when attached to different moving objects, may take on any of a number of forms. For example, a housing including some or all of the components may be attached in strategic locations on or in such moving targets depending upon the nature of the motion being studied.

Referring to FIGS. 4A-4I, non-limiting example of signals containing motion data are depicted. FIGS. 4A-4I show exemplary direct sensor signals after having gone through analog to digital conversion and digital filtering stages. The top row of three graphs (FIGS. 4A, 4B and 4C) include acceleration data collected from an accelerometer, the first in the X direction, the second in the Y direction and the third in the Z direction. The middle row of three graphs (FIGS. 4D, 4E and 4F) include angular velocity data collected from a gyroscope the first in the X direction, the second in the Y direction and the third in the Z direction. The bottom row of three graphs (FIGS. 4G, 4H and 4I) include orientation data collected from a magnetometer, the first in the X direction, the second in the Y direction and the fourth in the Z direction. On each of the exemplary graphs, the Y axis is magnitude for standard units for acceleration m/s$^2$, angular velocity (degrees/sec) and orientation (degrees), and the X axis is time. In the depicted example, the time interval is set at 50 ms.

The disclosed computer program includes instructions that process motion data in particular units of motion. The number of data points x in the content of a particular unit of motion is the product of the number n of the degrees of freedom of motion being sensed and predetermined time intervals. Each data point x has affiliated strength information S, sometimes referred to as weight in the machine learning literature in the field of speech recognition. See, for example, US Patent Application Publication 2012/006,976 (now U.S. Pat. No. 8,972,253), both of which are incorporated by reference in their entireties.

In FIGS. 4A-4I, there are nine degrees of freedom being sensed and measured: X, Y and Z input for each of acceleration, angular velocity and orientation. There are predetermined time intervals of 50 ms. Each unit of motion in the example has 450 data points x. The content of a particular unit of motion (e.g., the data of unit of motion for the first 50 ms) reflects for that time period: acceleration in the X direction, acceleration in the Y direction, acceleration in the Z direction, angular velocity in the X direction, angular velocity in the Y direction, angular velocity in the Z direction, orientation in the X direction, orientation in the Y direction, and orientation in the Z direction.

The content of each real-time unit of motion is identifiable as being in a particular motion class with a library containing initial motion data. Where the content of a unit of motion is not close to fitting units of motion in a class, such high cost data need not be considered. Where a sensed unit of motion is close to more than one class, the strength information S indicates how close the content of a unit of motion fits one class as compared to another. Strength information is qualitative in this manner and can assist in focusing an algorithm on the most relevant data points x—the ones that have the lowest cost for fitting the sensed data to a particular non-linear equation (unit of motion) affiliated with a particular class. Unexpectedly, including more information in the content of a unit of motion can increase the accuracy, efficiency and performance of same for classification in the context of motion data.

Mathematical representations of the individual equations in the example and the function of the exemplary nine equations are below:

$$\text{Unit of motion} = f(S, x, n)$$

where
S is a matrix of unique strength numbers
x is a matrix of values from sensor output signals (9 degrees of freedom)
n is the number of motion classes
As a representation in the human example
n=5 (walking, running, jumping, biking, climbing)
x=450 values (9 signals×50 ms)
S=450×n=2250 unique numbers
Example representation is
Equation for unit of motion$_1=$
$$S_{1,0}*x_1 + S_{1,1}*x_2 + S_{1,2}*x_3 + S_{1,450}*X_{450}$$

Equation for unit of motion$_2=$
$$S_{2,0}*x_1 + S_{2,1}*x_2 + S_{2,2}*x_3 + S_{2,450}*x_{450}$$

In the human example, when the unit of motion is populated with data, the content of a given unit of motion may be unique to, for example, walking. The content of unit of motion 1 in real-time may be identifiable "walking," if the real-time data in the unit of motion closely matches that of one of the initial walking units of motion that are stored in a motion library, The content of unit of motion 2 may indicate "jumping." A motion class often has multiple units of motion that map to that class, but a particular unit of motion generally maps best to only one class or at least better to one class than another. Many detected motions, if the content of the unit of motion is not close to the content of a unit of motion in a predetermined class, are simply ignored because of the strength information S, permitting the processor and/or software to address lower cost motion data.

The computer program or collection of programs or modules disclosed herein compares real-time motion data, by unit of motion, to initial motion data for qualification and quantification of the real-time motion data. Initial motion data is gathered through actual sensed motion data. That is, initial motion data is real data; it is not a mere statistical model representing data.

One way of making and/or using the disclosed systems and devices and software is to employ one or more of the machine learning algorithms known to those of ordinary skill in the art. In such an algorithm, in a first instance, initial motion data is gathered, classified and/or stored as units of motion as part of a "training" process. That initial motion data may remain static unless or until a user updates that data through a "learning" process that the software is adapted to perform. This may be done, for example, where a moving target is outside a standard deviation of 95% of a population for like moving targets. In such case, machine learning can permit updating of the initial motion data for later comparison to real-time motion data. In one embodiment, such updating may occur automatically, perhaps at predetermined time intervals. Other purposes for re-populating the initial data values are contemplated, as are methods for so doing, whether manual or automatic or partly both. See, for example, the US patent application publication and later-issued US patent referenced and incorporated by reference above.

Figure 5:
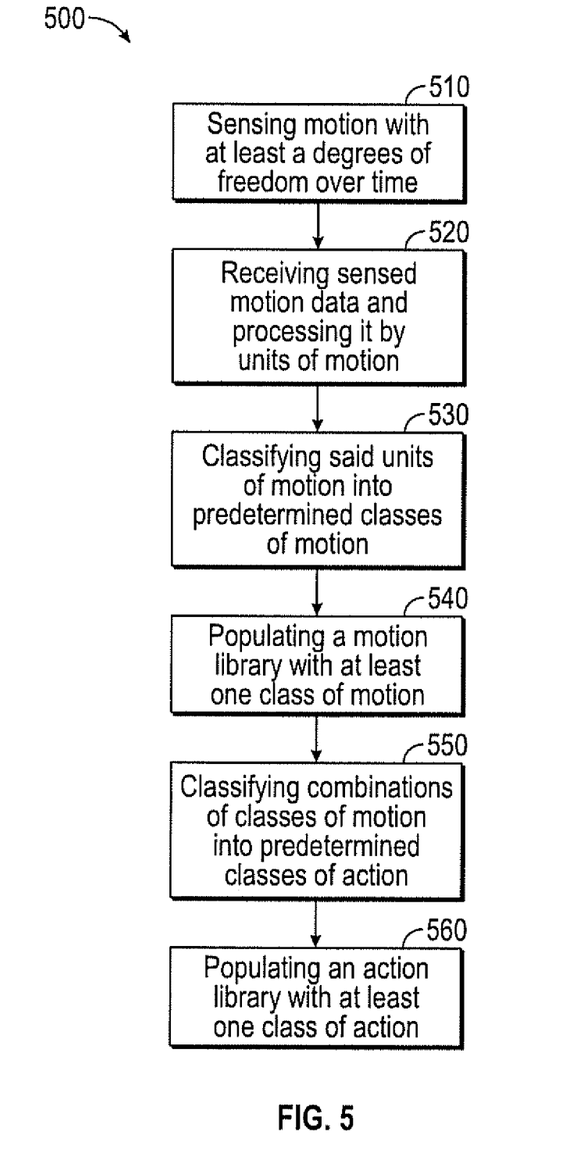
FIG. 5 is an exemplary flow chart for populating a motion library and an action library.

Referring to FIG. 5, a non-limiting exemplary process 500 is disclosed for "training" where a human being is the moving target as in the example of FIGS. 4A-4I. Different forms of training in the context of machine learning are known to skilled artisans, and those are also contemplated for use with the disclosed embodiments, as are different moving targets. In box 510, to gather the initial motion data, data is received from a plurality of signals emanating from a sensing system, thereby providing data to be processed in units of motion that are a non-linear equation for at least nine degrees of freedom over a predetermined time interval—50 ms time intervals. Depending on what type of motion is being sensed, different time intervals can be selected. For example, time intervals of 500 ms, 250 ms, 100 ms, 50 ms, 25 ms and 10 ms are some of the many contemplated time intervals for various human motions being analyzed.

In box 520, the sensed initial motion data is received and processed as units of motion. In the particular non-limiting example, each unit of motion includes 450 data points—the product of the degrees of freedom and the selected time interval. The content in each unit of motion is the data-populated equation that is the function of the nine separate equations, one for each degree of freedom being measured.

In box 530, the sensed initial motion data is classified by instructions in a computer program into predetermined classes of motion. In the human example, a set of predetermined classes of motion may include "walk" and "jump." Predetermined classes of motion may be chosen depending upon intended application and intended moving targets. For example, where an automobile is a moving target, predetermined classes may include "driving forward," "turning right," "turning left," "changing lanes," "accelerating," etc. Classifying the particular units of motion into such classes during learning can be done using any of a number of methods, including statistical models including but not limited to Hidden Markov Models (HMM).

In particular, the steps recited in boxes 520 and 530 may occur simultaneously or contemporaneously by using a context-dependent, pre-trained deep neural network HMM to extract from the plurality of motion signals the particular unit of motion for classification. Context-dependent, deep neural network HMM (CD-DNN-HMM) architectures may be used. Referring to the machine learning terminology of the above-referenced US Patent Application Publication and Patent, a CD-DNN-HMM may be used to estimate the posterior probability of a continuous density HMM's state. That is, the architecture provides the rubric to determine whether particular units of motion should be classified into one class or another or at all.

The posterior probability maybe modeled as $$p(S_i, C_j | x_t) = p(S_i | x_t) \, p(c_j | s_j, x_t)$$

where $x_t$ is a particular signal observed at time t, $c_j$ is one of the clustered context classes $C = \{c_1, \ldots, c_j\}$, $s_i$ is either a context-independent action or a state in a context-independent action. Artificial neural networks (ANNs) may be used to estimate $p(s_i | x_t)$ and $p(c_j | s_j, x_t)$ (alternatively $p(c_i | x_t)$ and $p(s_i | c_j, x_t)$).

In the depicted human example, each HMM represents a class like "walk" or "jump." An HMM includes several states and transitions between these states. Associated with each state i is an output distribution, $b_{i()}$, representing a distinct motion (unit of motion) from the data received by the series of signals. Restated, each output distribution (state) in an HMM describes a certain class of motion representing in the unit of motion as exemplified containing 450 data points that identify the content of that unit to be of a certain class. The output probability can be a combination of continuous probability density functions, a discrete probability distribution or a semicontinuous density function.

In certain embodiments, a forward-backward algorithm may be used to iteratively reestimate both output and transition probabilities. In some embodiments, the Viterbi beam search algorithm may be used during recognition to determine the most likely motion class.

In box 540, a step of populating a motion library having at least one initial motion class is described. Step 540 can be simultaneous with or contemporaneous with steps 520 and/or 530. Once the content of specific units of motion are identified as belonging to a particular class, the actual initial motion data (not statistical representations thereof) can be stored, organized and/or presented by units as being of a particular class within a greater construct of a "library." A library can be any of a number of data constructs, including but not limited to a table, a database, or other arrangement. Because the actual data is retained, so are all of its attributes that were collected. That might be time, height, distance, yaw, etc, depending upon what was collected for what type of motion. The initial motion data is available for comparison, qualification and/or quantification.

For example, in the depicted human example, a plurality of units of motion, each having 450 data points x at least some of which are distinct from one another, each independently signify walking. Each of those units, then, would populate the "walking" class. Another plurality of units of motion with different content might populate a "jumping" class. Each of a set of predetermined classes (walking, jumping, bursting, etc.) can be a part of a motion library. The motion library may be stored in any form of memory/computer readable media. The motion library can be local to or remote from, in whole or in part, the computing device so long is the software affiliated with the computing device can access the data in the library and its classes.

In box 550, the step of classifying combinations of classes of motions into more complex "actions" occurs. An action is a known, distinguishable qualitative set of motions. The process of classifying at the action level can be similar to the one used for classifying particular units of motion into motion classes. For example, a combination of units of motion in different classes all happening at a particular rate within a particular time frame might indicate that a human user is playing tennis. Tennis can be a predetermined action class. A different set of units of motion in different classes happening within a particular time frame might indicate that a human user is boxing. Boxing can be another predetermined action class.

In box 560, a step of populating an action library having at least one initial action class is described. Step 560 can be simultaneous with or contemporaneous with steps 520, 530, 540 and/or 550. Once the content of a combination of units of motion of one or more classes are identified as belonging to a particular action class, the actual initial motion data (not statistical representations thereof) can be stored, organized and/or presented by units as being of a particular class within a greater construct of an action library. The action library can be local to or remote from, in whole or in part, the computing device so long is the software affiliated with the computing device can access the data in the library and its action classes. The initial action data is available for comparison, qualification and quantification.

Figure 6:
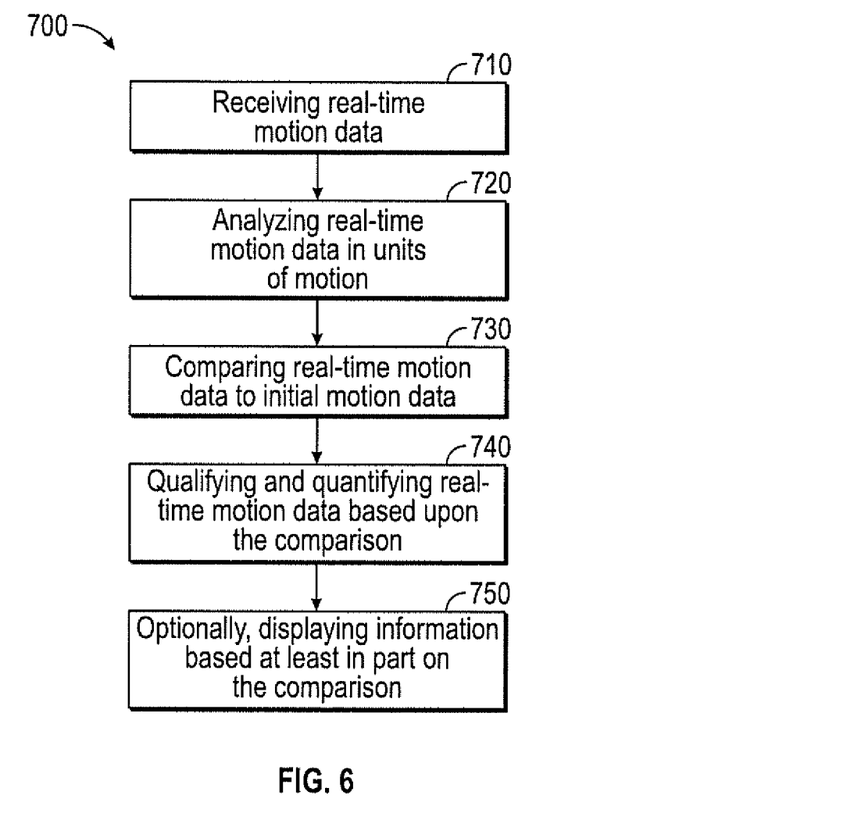
FIG. 6 is an exemplary flow chart for qualifying and quantifying real-time motion data as compared to data stored in a motion library.

Referring to FIG. 6, an exemplary method 700 of processing real-time motion data is disclosed. In box 710, real-time motion data is received from, directly or indirectly, a sensing system including sensing devices that generate signals for, at least, acceleration and angular velocity. Data is extracted from the signal; the software is configured to receive it for processing by a processor using at least computer program.

In box 720, using a processor, real-time motion data is processed or formatted as units of motion with the same degrees of freedom and in the same time interval to be useful for comparison against the initial motion data. Strength information for each data point in each unit of motion may be kept.

In box 730, using a processor, real-time motion data is compared against initial motion data in the motion library and in the action library. Real-time units of motion (or collections of same) compared against initial units of motion (or collections of same) for qualification and quantification, as referenced in box 740. The strength information may contribute to efficient processing of data.

Regarding qualification, a real-time unit of motion is recognized as, for example, a walk class unit of motion through comparison units of data in the walk class of the motion library. From there, quantification is possible, both of the real-time data and comparisons with the initial data. For example, the real-time "walk" is happening at a particular cadence, which is certain percentage faster than the initial data; the real-time walk involves a particular degree of pronation, which is a particular percentage greater or less than the initial data; etc.

Similarly, if a combination of certain units of motion in one or more classes of motion are sensed in real-time within a certain time period, that combination can be compared to the initial action classes in the action library for qualifying and quantifying an action. That is, if human performs a certain number of bursts and jumps within a certain time period; that combination can be qualitatively identified as a boxing action. From there, quantification is possible, both of the real-time data and comparisons with the initial data. For example, the real-time "boxing" is happening at a particular cadence, which is certain percentage slower than the initial data; the real-time boxing involves a particular pattern of bursts, which is a particular percentage greater or less than the initial data; etc.

Optionally, in box 750, information reflecting at least some of the qualification and/or quantification of the real-time motion data and of comparisons of the real-time motion data to initial motion data may be displayed on a any of a number of local or remote display mechanisms. Displays may include a screen or projection on a wearable device that includes at least part of a computing device, a smartphone screen, a tablet screen, an independent monitor, a laptop screen and/or a desktop screen.

Figure 7:
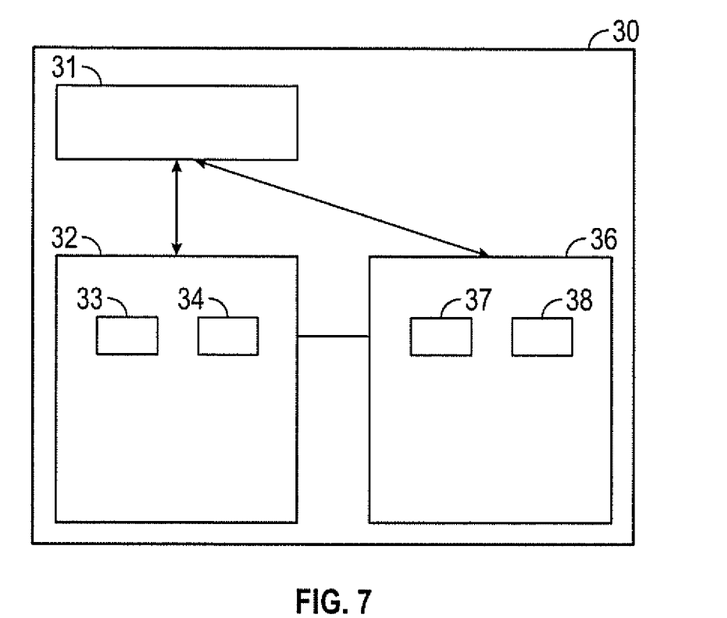
FIG. 7 is a schematic representation of an exemplary computer program accessing data in one or more libraries for comparison to real-time motion data.

Referring to FIG. 7, an exemplary schematic of memory/computer readable media 30 used by a processor in connection with the computing device is provided. Box 31 indicates software, operating in an operating system, with instructions capable of controlling one or more processors to performing the steps of the training methods 500 or the analyzing methods 700. The software program 31 can be a unitary program or represent a number of modules in communication with one another. The software program 31 may also be configured to machine "learn" based upon real-time data, which is a process much like training except that it occurs when activated by a user and/or automatically.

The software program 31 is in communication with motion library 32 and action library 36. Within motion library 32, motion class 33 and motion class 34 are shown. Within action library 36, action class 37 and action class 38 are shown. Although boxes are represented as unitary, it is contemplated that libraries 32 and/or 36 may be remote from the particular memory/computer readable media 30 upon which program 31 is running, so long as program 31 is able to communicate with the libraries 32 and 36 and access the data therein.

Figure 8:
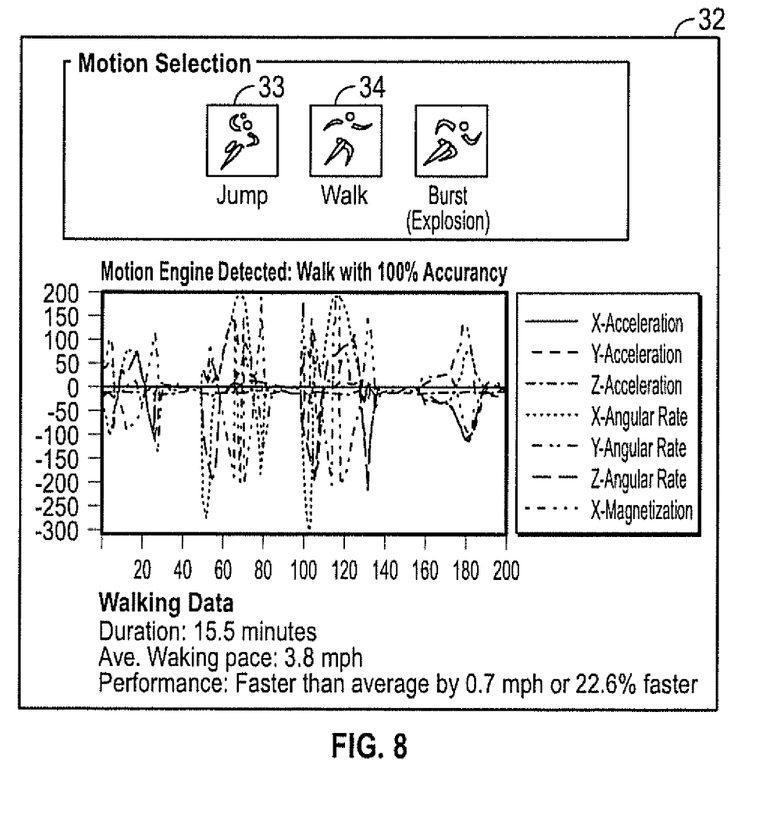
FIG. 8 is an example of a display of a motion library.

FIG. 8 is an exemplary display on a screen of a motion library 32. Motion classes 33 and 34 are for jumping and walking. In the depicted embodiment, the confidence of identity of the particular motion (qualification) is displayed, as well as a window showing a plurality of distinct units of motion all linked to walking. Quantification data may also be shown, including data such as time spent walking, distance covered, etc. Information may be displayed to convey any combination of underlying data relating to one or more of the real-time motion data. Additional information may also be displayed, including heart rate, blood pressure, temperature, etc. if such information is also sensed with a sensing system that is as part of or in cooperation with the computing device.

Figure 9:
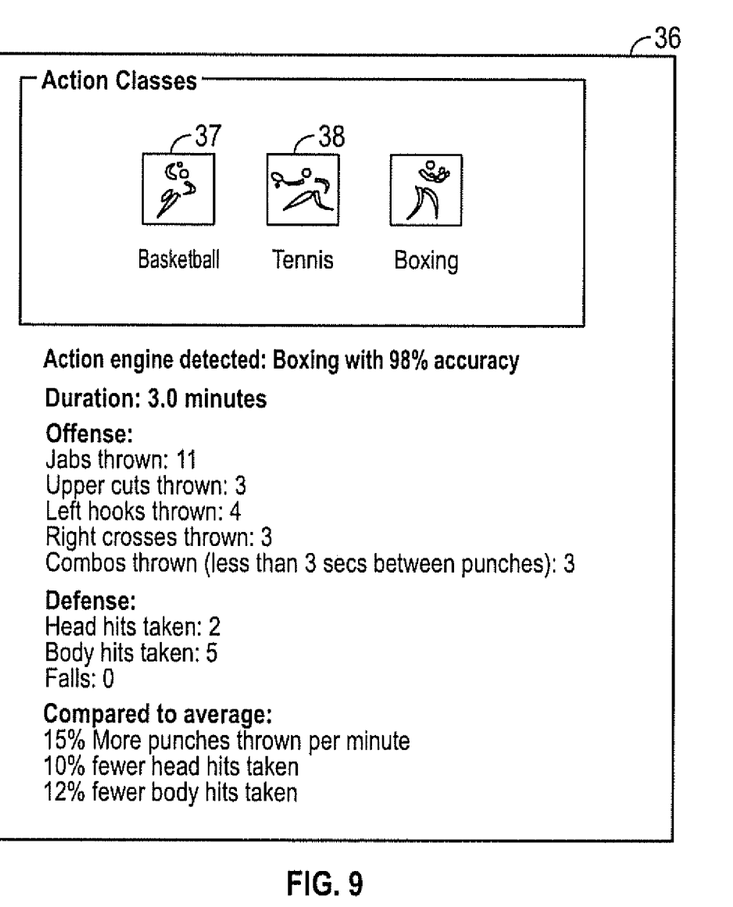
FIG. 9 is an example of a display of an action library.

FIG. 9 is an exemplary display on a screen of an action library 36. Action classes 37 and 38 for tennis and boxing, and another classes is for basketball. In the depicted embodiment, the confidence of identity of the particular action (qualification) is displayed, as well as a window showing a plurality of distinct units of motion all linked to walking. Quantification data may also be shown, including data such as time spent walking, distance covered, etc. Information may be displayed to convey any combination of underlying data relating to one or more of the real-time motion data. Additional information may also be displayed, including heart rate, blood pressure, temperature, etc. if such information is also sensed with a sensing system that is as part of or in cooperation with the computing device.

The disclosed systems, devices and methods can work with and in many operating environments, which can include one or more user computing devices and/or one or more processors. User or client devices can include any of a number of general purpose personal computers, such as wearable technologies and/or mobile and handheld devices with software that works with a number of networking and messaging protocols.

Disclosed processors and memory/computer-readable media can be local or remote. That is, some embodiments are local to a self-contained device and system, such as a wearable device (e.g., a wristwatch). Other embodiments are partially local and partially remote. For communication with remote devices of any kind, it is contemplated that at least one network or supporting communications using any of a number of protocols may be used, such as TCP/IP, FTP, OSI, NFS, UPnP, CIFS, and AppleTalk. The network can be, without limitation, a local area network, a wide-area network, a virtual private network, the Internet, the cloud, an intranet, an extranet, an infrared network, a wireless network, and any combination.

The disclosed systems, devices and methods also can be implemented, at least in part, as a service or Web service that may be part of a service-oriented architecture. Such services can communicate using any suitable form of messaging, such as by using messages in extensible markup language (XML) format and exchanged using a protocol such as SOAP ("Simple Object Access Protocol"). Processes provided by or executed by such services can be in any suitable language, including the Web Services Description Language (WSDL).

In systems using a Web server, the Web server can run any of a variety of servers, including HTTP servers, FTP servers, CGI servers, data servers, Java servers, and more. The servers may be capable of executing programs or scripts in response requests from user devices. The programs may be written in any programming language, such as Java, C, or C++, or any scripting language, such as Perl, Python, or TCL, as well as combinations. The servers may also include database servers, such as those available from Oracle and Microsoft.

The hardware and/or software environment of the disclosed systems and devices can include a variety of data stores and other memory and storage media. Such media can reside in any of a number of locations, such as on a storage medium local to (and/or resident in) one or more of the computing devices or remote from any or all of the computing devices across the network. In a particular set of embodiments, the information may reside in a storage-area network ("SAN"). Also, any necessary files for performing the functions attributed to the computers, servers, or other network devices may be stored locally and/or remotely. Where a system includes computerized devices, each device can include hardware components that may be electrically coupled via a bus. Such components may be, for example, at least one processor or microprocessor, at least one input device (e.g., a keyboard or touch screen), and at least one output device (e.g., a display device). Such a system may also include memory/computer readable media such as disk drives, optical storage devices, and solid-state storage devices, as well as removable media devices, memory cards, etc. Further examples include memory/storage media such as volatile and non-volatile, removable and non-removable media. Examples include RAM, ROM, PROM, EPROM, EEPROM, flash memory or other memory technology, CD-ROM, digital versatile disk (DVD) or other optical storage, magnetic cassettes, magnetic tape, magnetic disk storage or other magnetic storage devices, or any other medium which can be used to store the information and which can be accessed by the system, device or method.

The disclosed systems and devices also can include a computer-readable storage media reader, a communications device and working memory. The computer-readable storage media reader can be connected with, or configured to receive, a computer-readable storage medium, representing remote, local, fixed, and/or removable storage devices as well as storage media for temporarily and/or more permanently containing, storing, transmitting, and retrieving computer-readable information. The system and devices also may include software applications, modules, services, or other elements within at least one working memory device, including an operating system and application programs, such as a client application. Numerous variations are contemplated. Further, connection to other computing devices such as network input/output devices may be used.

With regard to the processes described herein, it should be understood that, although the steps of such processes, have been described as occurring in a certain sequence, such processes could be practiced with the described steps performed in an order other than the exemplary order. It further should be understood that certain steps could be performed simultaneously, that other steps could be added, or that certain steps described herein could be omitted. In other words, the descriptions of processes herein are provided for the purpose of illustrating certain embodiments, and should in no way be construed so as to limit the claimed invention.

Accordingly, it is to be understood that the above description is intended to be illustrative and not restrictive. Many embodiments and applications other than the examples provided would be apparent upon reading the above description. The scope of the invention should be determined with reference to the appended claims along with the full scope of equivalents to which such claims are entitled. It is anticipated and intended that future developments will occur, and that the disclosed systems and processes will be incorporated into such future embodiments. The invention is capable of modification and variation.

All terms used in the claims are intended to be given their broadest reasonable constructions and their ordinary meanings as understood by those knowledgeable in the technologies described herein unless an explicit indication to the contrary is made. Use of the singular articles such as "a," "the," "said," recite one or more of the indicated elements unless a claim recites an explicit limitation to the contrary.

What is claimed as new and desired to be protected by Letters Patent of the United States is:

1. A computing device [10] for analyzing motion of a moving target, the device comprising:
    a) a processor [20], computer-readable media [30], an accelerometer [11], a gyroscope [12], a magnetometer [13], each configured to be in direct or indirect communication with one another; and
    b) a computer program [31] including instructions executable by the processor to create a qualitative and quantitative motion analysis, the computer program comprising:
        i) software configured to access the computer-readable media [30] including at least one library [32] of at least one class of initial motion data, such data being processible as units of motion, each such unit of motion being an equation over a predetermined time interval that is a function of separate initial motion data equations for at least acceleration data, angular velocity data, and orientation data in a predetermined number of degrees of freedom, each such unit of motion retaining the quality and quantity of the initial motion data, each such unit of motion having content including a number of data points x equal to the product of the degrees of freedom by the predetermined time interval;
        ii) software configured to receive real-time motion data from sensed signals, the real-time motion data including at least acceleration data from the accelerometer [11], angular velocity data from the gyroscope [12], and orientation data from the magnetometer [13], such real-time motion data being processible in the same units of motion as the initial motion data;
        iii) software configured to compare, by units of motion, the real-time motion data to the initial motion data; and
        iv) software configured to qualify and quantify the real-time sensed motion data based at least in part upon the comparison, said unit of motion is an equation reflecting the function of equations at least of acceleration data in an X, Y, and Z direction, angular velocity data in an X, Y, and Z direction, and orientation data in an X, Y and Z directions totaling nine degrees of freedom over the predetermined time interval, the contents of the unit of motion comprising a number of data points x equal to the product of 9 degrees of freedom and the predetermined time interval, each data point having strength information S affiliated therewith, the strength information S indicating how close a content of a unit of motion fits one class compared to another; the strength information S is retained after classification for comparison between real time motion data and initial motion data in order to provide information to an algorithm about which motion data to ignore and which motion data to further analyze for qualification.

2. The computing device of claim 1, wherein the computer readable media [30] includes at least one library [36] of initial action data, where action data is a combination of classified initial motion data over a predetermined time interval.

3. The computing device of claim 2, wherein the computer readable media [30] includes at least one library [36] of initial action data, where action data is a combination of classified initial motion data occurring in a particular sequence over a predetermined time interval.

4. The computing device of claim 1, wherein real-time motion data is transmitted through at least one inertial measurement unit including at least one of the accelerometer [11], the gyroscope [12], and the magnetometer [13].

5. The computing device of claim 1, wherein real-time motion data further includes global positioning data sensed by a global positioning system in communication with the processor [20].

6. The computing device of claim 1, wherein real-time motion data is received through at least one processed signal generated by at least one of the accelerometer [11], the gyroscope [12], the magnetometer [13], where at least one of the accelerometer [11], the gyroscope [12], the magnetometer [13] is on or in a wearable device.

7. The computing device of claim 6, wherein the accelerometer [11], the gyroscope [12], the magnetometer [13], the computer readable media [30] and the processor [20] are local to the wearable device.

8. The computing device of claim 6, wherein at least a portion of the computer readable media [30] in communication with the processor [20] is remote to the wearable device.

9. The computing device of claim 6, further comprising a local or a remote display [400], wherein the display [400] is configured to show information reflecting at least a portion of qualification or quantification data.

10. The computing device of claim 1, wherein real-time motion data is received through processed signals generated by the accelerometer [11], the gyroscope [12], and the magnetometer [13], each of the accelerometer [11], the gyroscope [12], and the magnetometer [13] being local to a device directly or indirectly attachable to an animal, a vehicle, a robotic apparatus, a missile, and moving componentry of a machine.

11. The computing device of claim 1, wherein in the computer program [31] further includes software configured to update initial motion data by machine learning, replacing the initial motion data with real-time motion data.

12. The computing device of claim 1, further comprising a display [400] in communication with the processor [20].

13. A method of processing real-time motion data, comprising:
a) receiving real-time motion data from at least one signal from at least one sensing device [11, 12, 13] configured to sense at least one of acceleration data, angular velocity data and orientation data;
b) with a processor [20], analyzing real-time motion data in predetermined units of motion, each such unit of motion being an equation over a predetermined time interval that is a function of separate motion data equations for at least acceleration data, angular velocity data and orientation data in a predetermined number of degrees of freedom, each such unit of motion retaining the quality and quantity of the sensed motion data;
c) with a processor [20], comparing real-time units of motion against initial units of motion classified into classes of motion in computer-readable media [30], such initial units of motion being actual data rather than statistical models of actual data; and
d) with a processor [20], qualifying and quantifying the real-time motion data based upon, at least in part, the comparison, said unit of motion is an equation reflecting the function of separate equations of acceleration data in X, Y, and Z directions, angular velocity data in X, Y, and Z directions and orientation data in X, Y, and Z directions, totaling nine degrees of freedom over the predetermined time interval; the contents of the unit of motion, the contents of the unit of motion comprising a number of data points x equal to the product of 9 degrees of freedom and the predetermined time interval, each data point having a strength information affiliated therewith, the strength information S indicating how close a content of a unit of motion fits one class compared to another, the strength information is retained after classification for comparison between real-time motion data and initial motion data in order to provide information to an algorithm about which motion data to ignore and which motion data to further analyze for quantification.

14. The method of claim 13, further including displaying information based upon at least a portion of the qualification or quantification of the comparison on a display [400] that is local or remote from a device housing the at least one sensing device [11, 12, 13].

15. The method of claim 13 wherein the receiving step further includes receiving real-time positional data from at least one of a GPS sensor or an RFID sensor.

16. The method of claim 13 further comprising updating initial motion data with real-time motion data.

17. The method of claim 13 further comprising qualifying and quantifying real-time motion data as compared against stored initial motion data and stored initial action data, where an action is a combination of particular motions of one or more classes of motion.

* * * * *